(12) United States Patent
Hsieh

(10) Patent No.: US 6,452,996 B1
(45) Date of Patent: Sep. 17, 2002

(54) METHODS AND APPARATUS UTILIZING GENERALIZED HELICAL INTERPOLATION ALGORITHM

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 35 days.

(21) Appl. No.: 09/810,925

(22) Filed: Mar. 16, 2001

(51) Int. Cl.$^7$ ................................................. A61B 6/03
(52) U.S. Cl. .......................................... 378/15; 378/901
(58) Field of Search ................................. 378/4, 15, 99

(56) References Cited

U.S. PATENT DOCUMENTS

| | | | |
|---|---|---|---|
| 5,208,746 A | 5/1993 | King et al. | |
| 5,216,601 A | 6/1993 | Crawford et al. | |
| 5,233,518 A | 8/1993 | King et al. | |
| 5,270,923 A | 12/1993 | King et al. | |
| 5,546,439 A | 8/1996 | Hsieh | |
| 6,381,297 B1 * | 4/2002 | Hsieh | 378/15 |
| 6,404,842 * | 6/2002 | Hsieh | 378/15 |

* cited by examiner

Primary Examiner—David V. Bruce
(74) Attorney, Agent, or Firm—Carl B. Horton, Esq.; Armstrong Teasdale LLP

(57) ABSTRACT

Methods and Apparatus to reduce image artifacts when reconstructing an image with a multislice computed tomographic (CT) imaging scanner. An object is helically scanned to obtain a plurality of projection views of an object, a plane of reconstruction is defined, a conjugate sample line is defined that does not intersect the plane of reconstruction, a weighting function is applied to the conjugate samples to reduce image artifacts, and the image is reconstructed after the weighted data is filtered and back-projected. The method reduces potential image artifacts without requiring additional hardware be used or replaced.

31 Claims, 6 Drawing Sheets

METHODS AND APPARATUS UTILIZING GENERALIZED HELICAL INTERPOLATION ALGORITHM

BACKGROUND OF THE INVENTION

This invention relates generally to methods and apparatus for CT imaging and other radiation imaging systems and, more particularly, to utilizing a generalized helical interpolation algorithm.

In at least some "computed tomography" (CT) imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at a detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged, so the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent to the scintillator. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units," which are used to control the brightness of a corresponding pixel on a cathode ray tube display.

To reduce the total scan time required for multiple slices, a "helical" scan may be performed. To perform a "helical" scan, the patient is moved in a z-axis direction synchronously with the rotation of the gantry, while the data for a prescribed number of slices is acquired. Such a system generates a single helix from a fan beam helical scan. The helix mapped out by the fan beam yields projection data from which images in each prescribed slice may be reconstructed.

In some CT imaging systems, the detector array is segmented so that a plurality of quasi-parallel slices of projection data are acquired and processed to construct a plurality of images corresponding to several slices through a volume. Such CT imaging systems are referred to as "multislice" systems. Multislice systems provide more data compared to a single slice system for reconstructing an image. Weighting conjugate samples in multi-slice systems, similar to weighting samples in single slice systems, leads to a breakdown in image reconstruction when a large number of slices are considered.

For a single slice system, two measurements are used to interpolate/extrapolate data collected from a single rotation of the gantry onto a "plane of reconstruction" (POR). Measurements acquired at different source positions are known as "conjugate measurements." The conjugate measurements are used to generate a conjugate sample line. Multislice CT imaging systems increase the flexibility in choosing a row or a plurality of rows that provide data closest to the POR. This flexibility of choosing a row may exist at both ends of a given ray, i.e., for both conjugate measurements for the same ray through the patient. Pitches for which conjugate measurements are available are known as HQ pitches.

The POR line intersects the conjugate sample line at an intersection point. At the intersection point, a weight becomes in-deterministic because the weight at the POR line should be unity and the weight for the conjugate sample line should be zero. Known algorithms dynamically switch the interpolation pairs so that two samples that are located closest to the POR are used for interpolation to avoid in-determinacy. At the point of switching, however, discontinuity in the weights occur. This discontinuity, after filter and backprojection, leads to a periodic rippling pattern from the center region of the reconstructed image to the outer edge of field of view. Typically, as a method of compensation, a feathering technique is used to bridge gaps in the weights. Yet, image artifacts can not be avoided, since the filtering operation in the image reconstruction is essentially a derivative operator that enhances any small discrepancies in the interpolated samples.

BRIEF SUMMARY OF INVENTION

Methods and apparatus for a multislice computed tomographic (CT) imaging system to reduce image artifacts when reconstructing an image are provided. In an exemplary embodiment of the method, an object is helically scanned to obtain projection data for a plurality of projection views of the object, a plane of reconstruction is defined, a conjugate sample line is defined that does not intersect the plane of reconstruction, a weighting function is applied to the conjugate samples to reduce image artifacts, and the image is reconstructed after the weighted data is filtered and backprojected.

In another aspect, an imaging system includes a computer, a gantry having a detector array, an x-ray source for radiating an x-ray beam toward the detector array, and the imaging system acquires projection data for a plurality of projection views of the object, defines a plane of reconstruction, defines a conjugate sample line that does not intersect the plane of reconstruction, applies a weighting function to the conjugate samples to reduce image artifacts, and reconstructs the image after the weighted data is filtered and backprojected.

In another aspect, a processor in the imaging system is programmed to acquire projection data for a plurality of projection views of the object, define a plane of reconstruction, define a conjugate sample line such that it does not intersect the plane of reconstruction, apply a weighting function to the conjugate samples to reduce image artifacts, and reconstruct the image after the weighted data is filtered and backprojected.

In yet another aspect, a computer-readable medium in the imaging system is provided which comprises a plurality of records of projection data used to define a plane of reconstruction. In addition, a record of conjugate samples is stored on the computer-readable medium. A program residing on the computer-readable medium utilizes a plurality of rules to define a conjugate sample line based on the record of conjugate samples which does not intersect the plane of reconstruction. Further, the program includes a plurality of rules to determine a weighting function that is applied to the conjugate samples to reduce image artifacts and reconstruct the image.

DETAILED DESCRIPTION OF THE INVENTION

Figure 1:
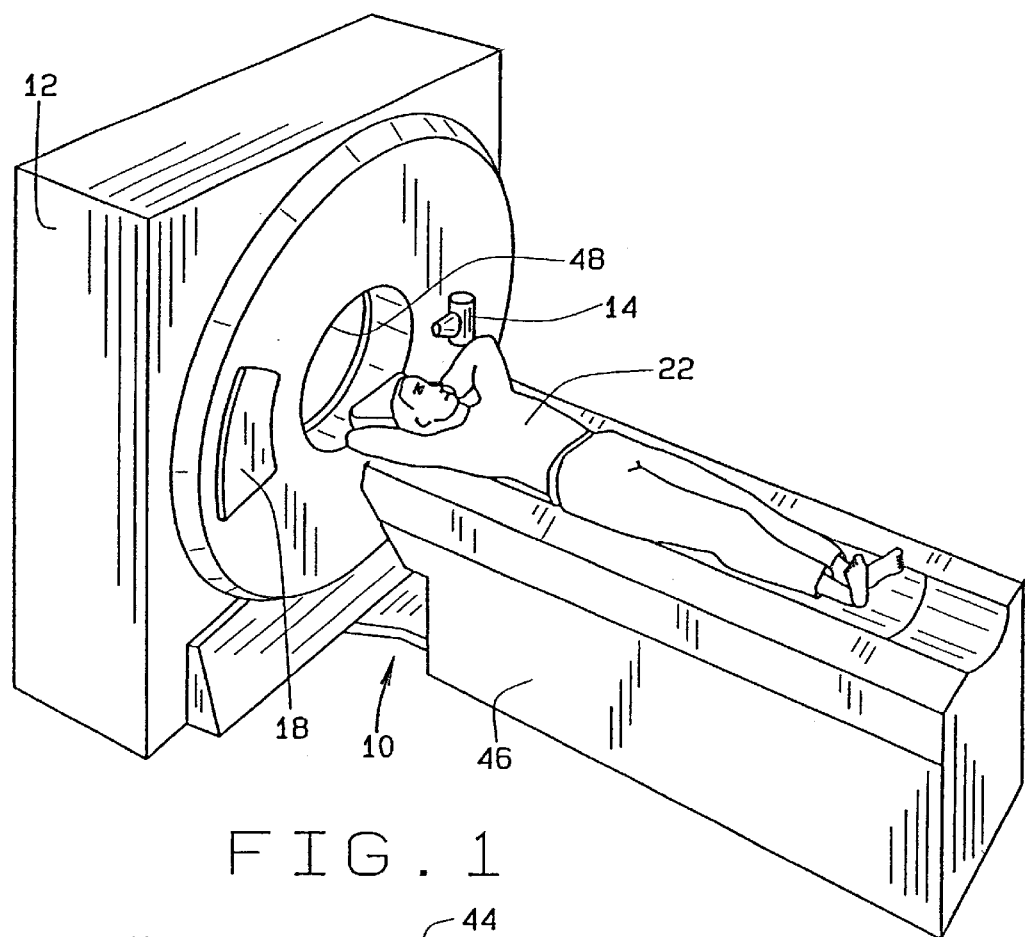
FIG. 1 is a pictorial view of a CT imaging system.
Figure 2:
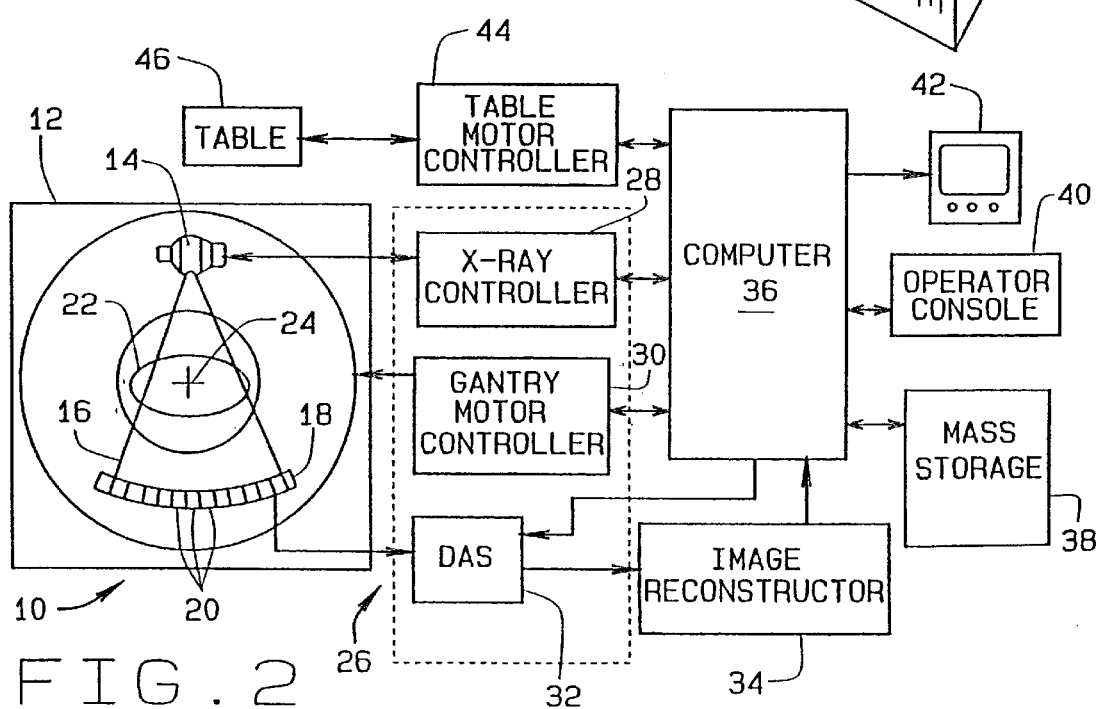
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-ray 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

When an HQ pitch is used, a CT imaging system is said to operate in "High Quality" (HQ) mode. For a given helical pitch in HQ mode, a set of Radon points exists for which the conjugate measurements are offset by approximately half of a detected aperture z. "Detector aperture" refers to an aperture on an isocenter associated with one "macro detector row," or one measurement. For example, in one known four-slice scanner with a detector angle γ equal to zero and a 3:1 pitch operating in HQ mode, the conjugate measurements are offset by Δz/2, i.e., half the aperture. In such a situation, a minimal z interpolation width is often used. However, this ideal sampling situation occurs only at a limited number of Radon points. The offset gradually departs from optimum, the further away from the isocenter. The greater the number of rows and correspondingly, the higher the pitch, the more rapid the departure from optimum.

A known eight-slice CT imaging system operating in HQ mode with either a 5:1 or a 7:1 helical pitch using known reconstruction techniques produce image artifacts in a periodic rippling pattern extending to an outer edge of a "field of view" (FOV) in the image rendering the images unsuitable for clinical usage. The image artifacts result from changes in the helical weights as a function of a detector angle, y. The change of the weights is caused by the combination of a faster table speed in an eight-slice scanner and a large slope angle formed by the conjugate samples to the POR. In a know reconstruction algorithm, POR is selected as a plane perpendicular to the table translation axis, and the POR can be described by the following linear relationship:

$$\beta=\beta_k, \qquad (1)$$

where $\beta_k$ represents the projection angle at which the detector row k intersects the POR. Based on the fan beam sampling geometry, the conjugate samples are located along the line:

$$\beta=\beta_k\pm\pi-2\gamma, \qquad (2)$$

where $\beta_k$ represents the projection angle at which the detector row k intersects the POR and γ is a detector angle. Equation (2) is the conjugate sample line, β', that describes the conjugate samples to the POR for all detector rows that form a set of sloped parallel lines. In a multi-slice helical CT, the conjugate samples to the POR of the detector row k are collected with detector rows other than k.

Figure 3:
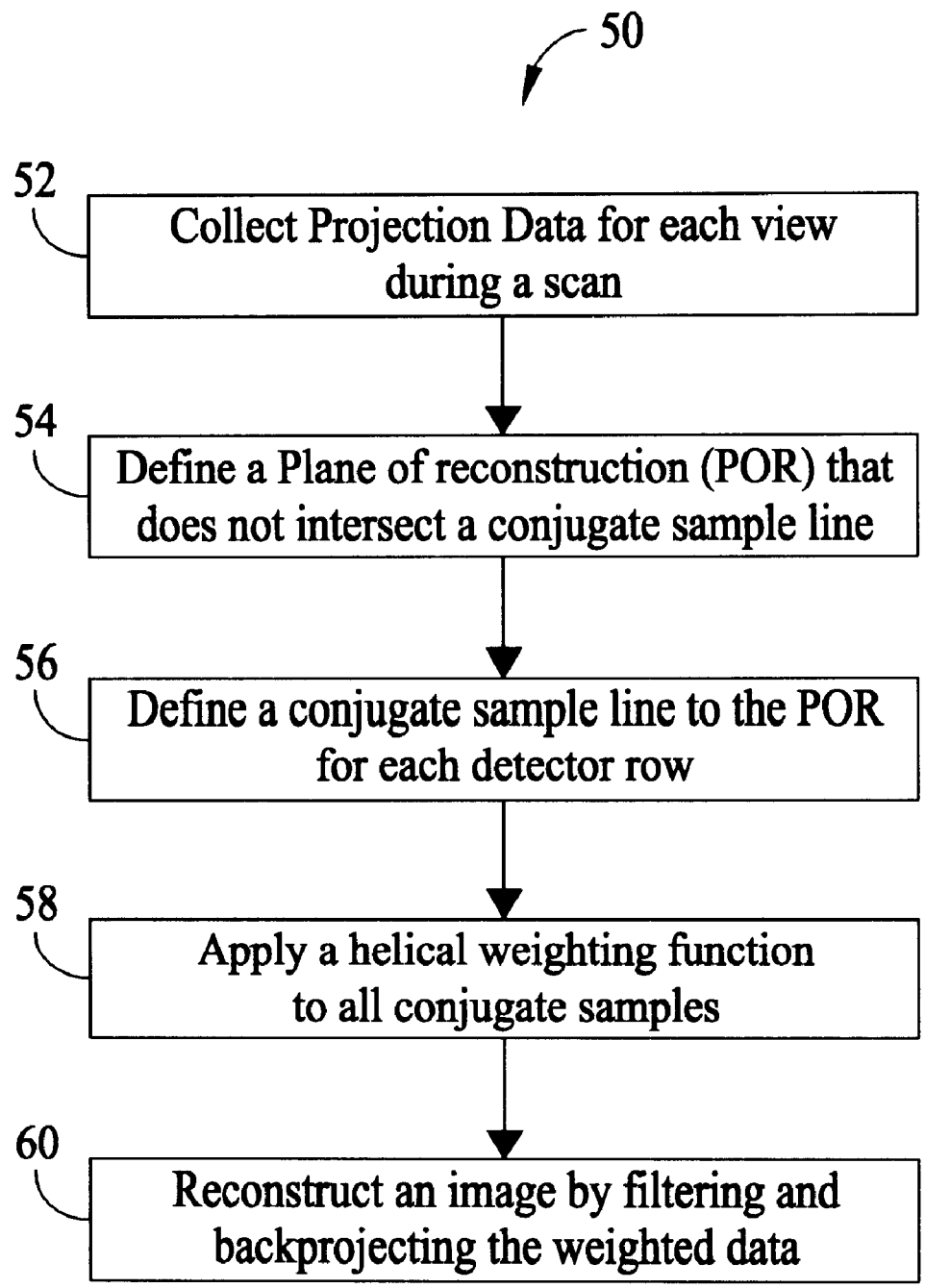
FIG. 3 is a flow chart illustrating the steps executed by the CT system to utilize a generalized helical interpolation algorithm.

FIG. 3 is a flow chart 50 illustrating the steps executed by CT system 10 (shown in FIG. 1) to reduce image artifacts generated by in deterministic intersection points. The method illustrated by flowchart 50 in FIG. 3 can be practiced by DAS 32 (shown in FIG. 2), image reconstructor 34 (shown in FIG. 2), or computer 36 (shown in FIG. 2). Generally, a processor in at least one of DAS 32, reconstructor 34, and computer 36 is programmed to execute the process steps described below. Of course, the method is not limited to practice in CT system 10 and can be utilized in connection with many other types and variations of imaging systems.

Referring specifically to FIG. 3, when performing a scan, a set of raw projection data is acquired 52, which is pre-processed to generate a set of projection view data. A plane of reconstruction is defined 54. A conjugate sample line is defined 56 that does not intersect the plane of reconstruction. When defining the POR and the conjugate sample line, a minimum value of α is selected to ensure the POR does not intersect the conjugate sample line. Image artifacts are eliminated when the POR does not intersect the conjugate sample line. The value of a should ensure a smooth weighting function. The weighting function should have no discontinuities and is applied 58 to all conjugate samples. An image is reconstructed 60 by filtering and backprojecting the weighted data.

Figure 4:
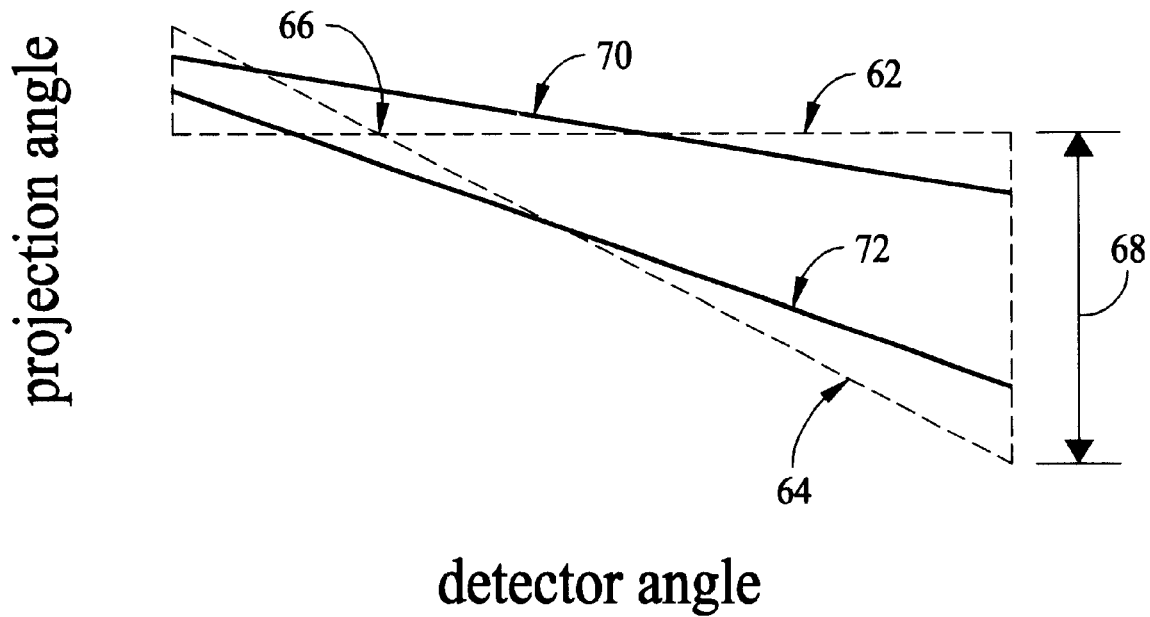
FIG. 4 is an illustration of POR and conjugate samples to the POR utilized by the generalized helical interpolation algorithm.

Referring to FIG. 4, a POR line 62 and conjugate sample line 64 form a triangle with base length 68 intersecting at intersection point 66. As illustrated, base length 68 represents an angular distance between POR line 62 and conjugate sample line 64. It is known for a 7:1 helical pitch, the angular distance is π/7 for an iso-ray. Similarly, for other helical pitches, various angular distances exist between the POR and the conjugate sample line. To avoid image artifacts caused by the intersection of POR line 62 and conjugate sample line 64, in one embodiment, a "new" POR line 70 is defined as a straight-line that does not intersect a conjugate sample line 72. Specifically, new POR line 70 is a tilted line with respect to a horizontal line in Radon space. Any potential image artifacts at intersection point 66 caused by a discontinuity in the weights during interpolation are avoided because new POR line 70 and conjugate sample line 72 do not intersect. Mathematically, new POR line 70, β, and conjugate sample line 72, β', are described by the following equations:

$$\beta = \beta_k - 60\gamma, \quad (3)$$

$$\beta = \beta_k \pm \pi - (2-\alpha)\gamma, \quad (4)$$

where $\beta_k$ represents the projection angle at which the detector row k intersects the POR when γ=0, γ represents a detector angle, and a represents a value that ensures new POR line 70 and conjugate sample line 72 do not intersect.

The minimum value of a that ensures the two lines do not intersect is $\alpha \geq 1-\pi/(2Q\gamma_m)$, where Q is a helical pitch. In one embodiment for a 7:1 helical pitch, $\alpha \geq 1-\pi/(14\gamma_m)$, where $\gamma_m$ is a maximum detector angle. For a Q:1 helical pitch, the minimum value of α is $$\alpha \geq 1 - \frac{\pi}{2Q\gamma_m}.$$

The value of α is kept to a minimum because large values of α indicate a large deviation of POR from an ideal POR. The ideal POR is a flat plane perpendicular to the table translation axis. Further, the value of α should ensure a smooth weighting function transition to avoid any potential image artifacts. In a preferred embodiment, α is 1.1 times the minimum value of $1-\pi/(14\gamma_m)$ for a 7:1 helical pitch, and for a Q:1 helical pitch α is 1.1 times the minimum value of $$1 - \frac{\pi}{2Q\gamma_m}.$$

For other helical pitches, a similar calculation is performed to estimate the minimum α value.

Figure 5:
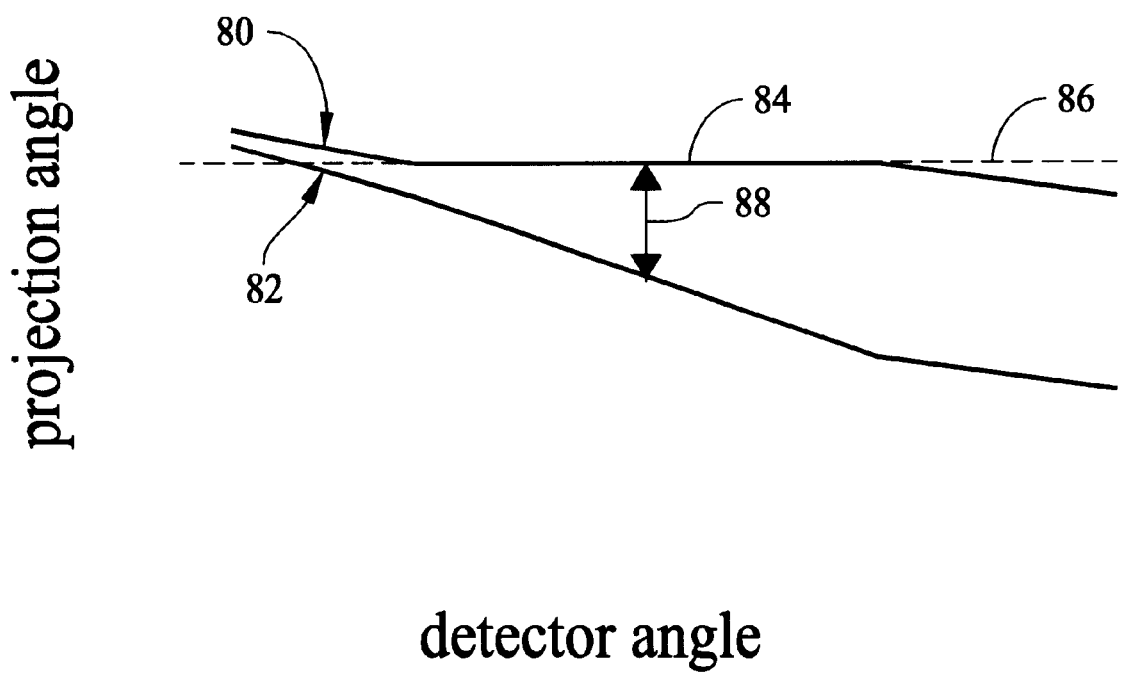
FIG. 5 is an illustration of a piecewise linear POR.

Referring specifically to FIG. 5 another POR line is defined as a piecewise POR line 80 and a conjugate sample line 82. In one embodiment, piecewise POR line 80 and conjugate sample line 82 are piecewise straight lines in sinogram space that do not intersect. Piecewise POR line 80 includes a portion 84 of an ideal POR line 86. For a 7:1 helical pitch, an angular distance 88 between piecewise POR line 80 and conjugate sample line 82 for an iso-ray is or π/7.

Figure 6:
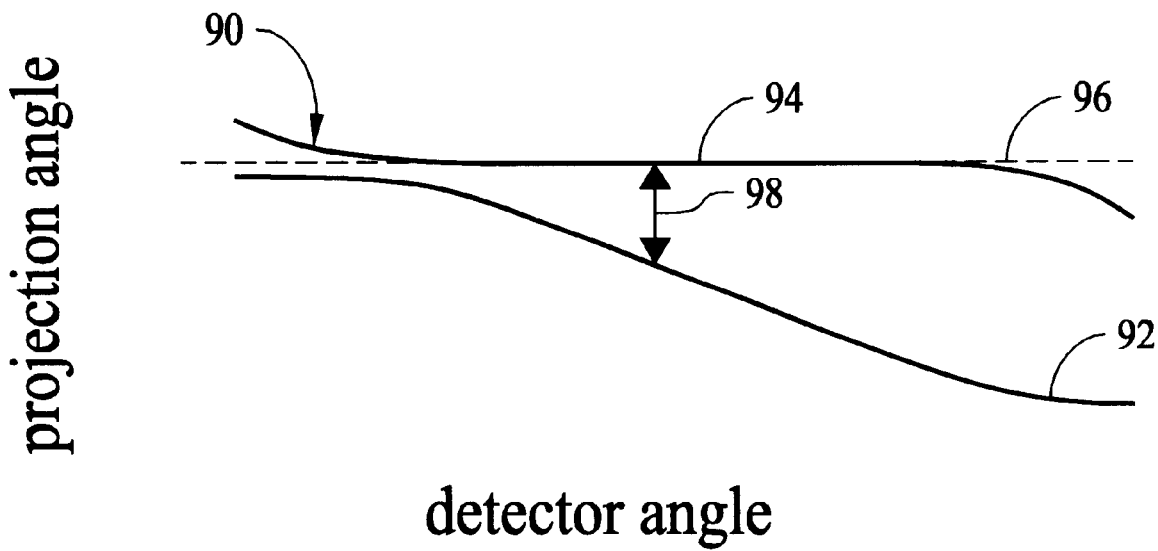
FIG. 6 is an illustration of a general curve POR.

Referring specifically to FIG. 6 yet another POR line is defined as curved POR line 90 and a conjugate sample line 92. Curved POR line 90 and conjugate sample line 92, in one embodiment, are curves in sinogram space that do not intersect. Curved POR line 90 includes a portion 94 of an ideal POR line 96. For a 7:1 helical pitch, an angular distance 98 between curved POR line 90 and conjugate sample line 92 for an iso-ray is or π/7.

In selecting a POR, an objective is to minimize utilizing the ideal flat plane POR. The shape of the POR can be tailored to a particular clinical application. For example, in the case of a head scan, the center 25 cm "field of view" (FOV) is the area of interest to be reconstructed. Therefore, a POR having a piecewise straight line design should be selected to minimize the deviation of the POR for the center 25 cm FOV. On the other hand, if the application requires an entire 50 cm FOV, a POR having a single straight line design should be selected.

Figure 7:
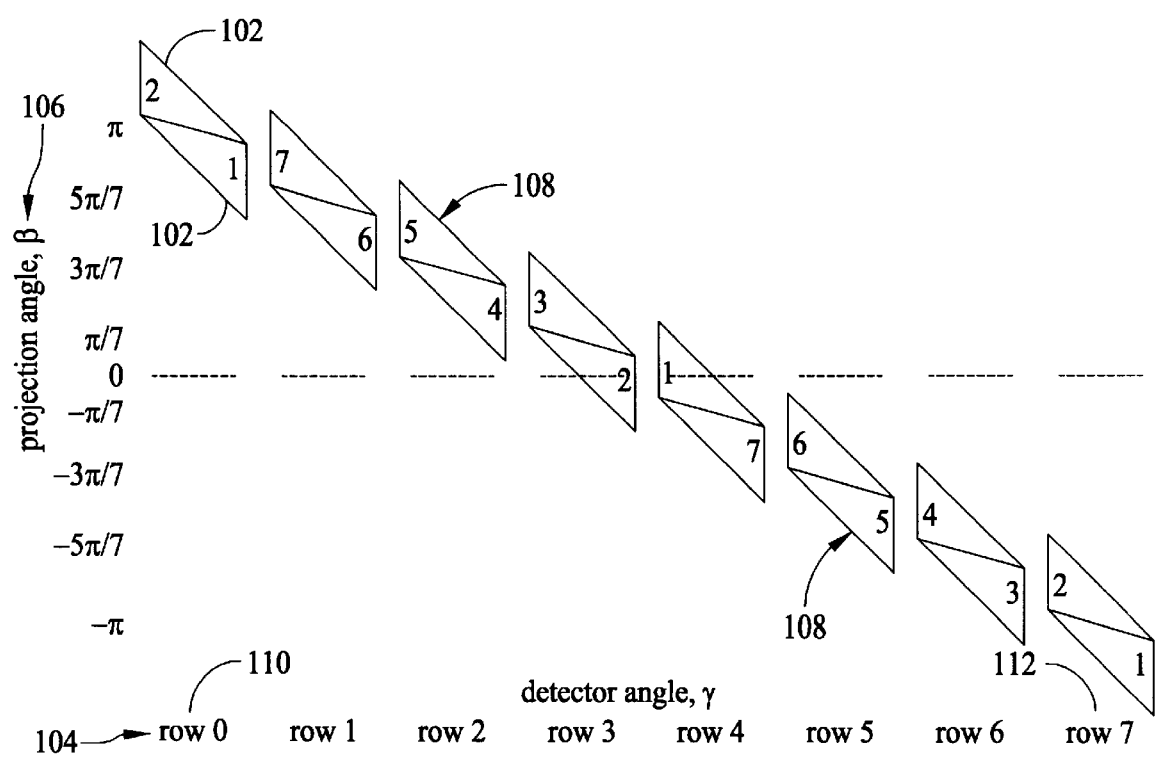
FIG. 7 is an illustration of conjugate sampling regions for 7:1 helical pitch.

Once the POR and the conjugate samples to POR are determined, a plurality of the helical weights are determined. Referring specifically to FIG. 7, a plurality of conjugate sampling regions 102 for a 7:1 helical pitch and a plurality of rows 104 plotted against a plurality of projection angles 106 are shown. A plurality of conjugate regions are labeled by identical numbers, e.g. conjugate region 108 is labeled as the number five. There is a 2π rotation delay, ignoring cone beam effect, between a first detector row 110 and a last detector row 112. Corresponding to the detector rows, there are three conjugate sampling regions.

A helical weighting function for each row can be described by the following relationship:

$$w_k(\gamma, \beta) = \begin{cases} \frac{\eta_k[\beta - \beta_{1,k}(\gamma, \beta)]}{\beta_{0,k}(\gamma, \beta) - \beta_{1,k}(\gamma, \beta)}, & \beta_{1,k}(\gamma, \beta) \leq \beta < \beta_{0,k}(\gamma, \beta) \\ \frac{\eta_k[\beta_{2,k}(\gamma, \beta) - \beta]}{\beta_{2,k}(\gamma, \beta) - \beta_{0,k}(\gamma, \beta)}, & \beta_{0,k}(\gamma, \beta) \leq \beta < \beta_{2,k}(\gamma, \beta), \\ 0, & \text{otherwise} \end{cases} \quad (5)$$

where $\beta_{0,k}(\gamma,\beta)$ is the POR for detector row k, e.g., in an exemplary embodiment $$\beta_{0,k}(\gamma, \beta) = \beta_k - \alpha\gamma = \frac{2(k-3.5)\pi}{Q} - \alpha\gamma;$$

$\beta_{1,k}(\gamma,\beta)$ is a sample collected before $\beta_{0,k}(\gamma,\beta)$ and represents a value on detector row k that is a conjugate to the POR of another row, e.g., in an $$\beta_{1,k}(\gamma, \beta) = \beta_k - \frac{\pi}{Q} - (2-\alpha)\gamma;$$

$\beta_{2,k}(\gamma,\beta)$ for k=0, . . . 7, is a sample on detector row k that is the conjugate to the POR of another row that is collected after $\beta_{0,k}(\gamma,\beta)$ e.g., in an exemplary embodiment $$\beta_{2,k}(\gamma, \beta) = \beta_k + \frac{\pi}{Q} - (2-\alpha)\gamma;$$

$\eta_k$ is a row dependent scaling factor equal to 0.5 for k=0 and k=7, the center view of reconstruction is defined as β=0, and Q is a helical pitch. For other k values, $\eta_k$ equals 1. In one embodiment, there is no discontinuity in the weighting function.

A simple linear interpolation is utilized, in one embodiment, for the estimation of helical weights. In an alternative embodiment, higher order interpolation functions can be selected for determining helical weights. For example, a weighting function, $\theta_k(\gamma,\beta)$, that is related to $w_k(\gamma,\beta)$ is described by the following relationship:

$$\theta_k(\gamma,\beta)=3w_k^2(\gamma,\beta)-2w_k^3(\gamma,\beta) \tag{6}$$

When selecting a weighting function, the total contribution from all conjugate samples sums to unity, the weighting function is continuous and the weighting function should be as smooth as possible in the y direction. Additional z-directional smoothing will further reduce residual image artifacts.

In yet another embodiment, CT system 10 includes a computer program residing on a computer-readable medium within mass storage 38 for reconstructing the image. The program includes a plurality of records of projection data used to define a plane of reconstruction. A plurality of rules define a conjugate sample line based on a record of conjugate samples. The program utilizes a plurality of rules to ensure the plane of reconstruction does not intersect the conjugate sample line. In addition, the program includes a plurality of rules to determine a weighting function that is applied to the conjugate samples to reduce image artifacts, and reconstruct the image.

While the invention has been described in terms of various specific embodiments, those skilled in the art will recognize that the invention can be practiced with modification within the spirit and scope of the claims.

What is claimed is:

1. A method for reconstructing at least one image representative of an object with an imaging system, said method comprising the steps of:
   scanning an object to acquire a plurality of projection views of the object;
   defining a plane of reconstruction such that a conjugate sample line does not intersect the plane of reconstruction;
   applying a weighting function to the conjugate samples to reduce image artifacts; and
   reconstructing the image after filtering and backprojecting the data.

2. A method in accordance with claim 1 wherein said step of defining a plane of reconstruction further comprises the step of selecting the plane of reconstruction to be defined by at least one of a linear relationship, a piecewise straight line, and a curve.

3. A method in accordance with claim 2 wherein said linear plane of reconstruction comprises the relationship:

$$\beta=\beta_k-\alpha\gamma,$$

where $\beta$ is the plane of reconstruction, $\beta_k$ represents a projection angle at which a detector row k intersects the plane of reconstruction when $\gamma=0$, $\alpha$ is a value that ensures the plane of reconstruction and a conjugate sample line do not intersect, and $\alpha$ is defined as $\alpha \geq 1-\pi/(2Q\gamma_m)$ where Q is a helical pitch, $\gamma_m$ is a maximum detector angle, and $\gamma$ is a detector angle.

4. A method in accordance with claim 1 wherein said conjugate sample line comprises the relationship:

$$\beta'=\beta_k\pm\pi-(2-\alpha)\gamma,$$

where $\beta'$ is a conjugate sample line, $\beta_k$ represents a projection angle at which a detector row k intersects the plane of reconstruction when $\gamma=0$, $\alpha$ is a value that ensures the plane of reconstruction and the conjugate sample line do not intersect, and $\alpha$ is defined as $\alpha \geq 1-\pi/(2Q\gamma_m)$, where Q is a helical pitch, $\gamma_m$ is a maximum detector angle, and $\gamma$ is a detector angle.

5. A method in accordance with claim 1 wherein said step of applying a weighting function comprises the step of defining a helical weight according to the relationship:

$$w_k(\gamma, \beta) = \begin{cases} \dfrac{\eta_k[\beta-\beta_{1,k}(\gamma, \beta)]}{\beta_{0,k}(\gamma, \beta)-\beta_{1,k}(\gamma, \beta)}, & \beta_{1,k}(\gamma, \beta) \leq \beta < \beta_{0,k}(\gamma, \beta) \\ \dfrac{\eta_k[\beta_{2,k}(\gamma, \beta)-\beta]}{\beta_{2,k}(\gamma, \beta)-\beta_{0,k}(\gamma, \beta)}, & \beta_{0,k}(\gamma, \beta) \leq \beta < \beta_{2,k}(\gamma, \beta), \\ 0, & \text{otherwise} \end{cases}$$

where $w_k(\gamma,\beta)$ is the helical weight; $\beta_{0,k}(\gamma,\beta)$ is the POR for detector row k; $\beta_{1,k}(\gamma,\beta)$ is a sample collected before $\beta_{0,k}(\gamma,\beta)$ and represents a value on detector row k that is a conjugate to the POR of another row; $\beta_{2,k}(\gamma,\beta)$ for k=0, ... 7, is collected after $\beta_{0,k}(\gamma,\beta)$ and is a sample on detector row k that is the conjugate to the POR of another row; $\eta_k$ is a row dependent scaling factor equal to 0.5 for k=0 and k=7; the center view of reconstruction is defined as $\beta=0$, and Q is a helical pitch. For other k values, $\eta_k$ equals 1.

6. A method in accordance with claim 5 wherein said step of applying a weighting function comprises the step of determining a weighting function according to the relationship:

$$\theta_k(\gamma,\beta)=3w_k^2(\gamma,\beta)-2w_k^3(\gamma,\beta),$$

where $\theta_k(\gamma,\beta)$ is the weighting function, and $w_k(\gamma,\beta)$ is the helical weight.

7. A method in accordance with claim 1 wherein scanning an object comprises the step of helically scanning a volume of the object with a pitch that varies during the scan.

8. An imaging system comprising a computer, a gantry having a detector array, an x-ray source for radiating an x-ray beam along an imaging plane toward a detector array including a plurality of detector cells, the computer coupled to the x-ray source and the gantry, said imaging system configured to:
   scan an object to acquire a plurality of projection views of an object;
   define a plane of reconstruction such that a conjugate sample line does not intersect said plane of reconstruction;
   apply a weighting function to said conjugate samples to reduce image artifacts; and
   reconstruct at least one image of the object.

9. An imaging system in accordance with claim 8 wherein said plane of reconstruction comprises least one of a linear relationship, a piecewise straight line, and a curve.

10. An imaging system in accordance with claim 9 wherein said imaging system further configured to determine said linear plane of reconstruction according to the relationship:

$$\beta=\beta_k-\alpha\gamma,$$

where $\beta$ is the plane of reconstruction, $\beta_k$ represents a projection angle at which a detector row k intersects said plane of reconstruction when $\gamma=0$, $\alpha$ is a value that ensures said plane of reconstruction and said conjugate sample line do not intersect, and $\alpha$ is defined as $\alpha \geq 1-\pi/(2Q\gamma_m)$, where Q is a helical pitch, $\gamma_m$ is a maximum detector angle, and $\gamma$ is a detector angle.

11. An imaging system in accordance with claim 8 wherein said imaging system further configured to determine said conjugate sample line according to the relationship:

$$\beta' = \beta_k \pm \pi - (2-\alpha)\gamma,$$

where $\beta'$ is a conjugate sample line, $\beta_k$ represents the projection angle at which the detector row k intersects said plane of reconstruction when $\gamma=0$, $\alpha$ is a value that ensures said plane of reconstruction and said conjugate sample line do not intersect, and $\alpha$ is defined as $\alpha \geq 1 - \pi/(2Q\gamma_m)$, where Q is a helical pitch, $\gamma_m$ is a maximum detector angle, and $\gamma$ is a detector angle.

12. An imaging system in accordance with claim 8 wherein said weighting function comprises a helical weight according to the relationship:

$$w_k(\gamma,\beta) = \begin{cases} \dfrac{\eta_k[\beta - \beta_{1,k}(\gamma,\beta)]}{\beta_{0,k}(\gamma,\beta) - \beta_{1,k}(\gamma,\beta)}, & \beta_{1,k}(\gamma,\beta) \leq \beta < \beta_{0,k}(\gamma,\beta) \\ \dfrac{\eta_k[\beta_{2,k}(\gamma,\beta) - \beta]}{\beta_{2,k}(\gamma,\beta) - \beta_{0,k}(\gamma,\beta)}, & \beta_{0,k}(\gamma,\beta) \leq \beta < \beta_{2,k}(\gamma,\beta), \\ 0, & \text{otherwise} \end{cases}$$

where $w_k(\gamma,\beta)$ is said helical weight; $\beta_{0,k}(\gamma,\beta)$ is the POR for detector row k; $\beta_{1,k}(\gamma,\beta)$ is a sample collected before $\beta_{0,k}(\gamma,\beta)$ and represents a value on detector row k that is a conjugate to the POR of another row; $\beta_{2,k}(\gamma,\beta)$ for k=0, ... 7, is collected after $\beta_{0,k}(\gamma,\beta)$ and is a sample on detector row k that is the conjugate to the POR of another row; $\eta_k$ is a row dependent scaling factor equal to 0.5 for k=0 and k=7; the center view of reconstruction is defined as $\beta=0$, and Q is a helical pitch. For other k values, $\eta_{k \; equals}$ 1.

13. An imaging system in accordance with claim 8 wherein said weighting function comprises the relationship:

$$\theta_k(\gamma,\beta) = 3w_k^2(\gamma,\beta) - 2w_k^3(\gamma,\beta),$$

where $\theta_k(\gamma,\beta)$ is said helical weighting function, and $w_k(\gamma,\beta)$ is said helical weight.

14. An imaging system in accordance with claim 8 further configured to scan a volume of the object with a pitch that varies during the scan.

15. A processor programmed to reduce image artifacts in a computed tomography system, said processor configured to:

scan a volume of an object with a varying pitch to acquire a plurality of projection views of an object;

define a plane of reconstruction comprising a mathematical relationship such that a conjugate sample line does not intersect said plane of reconstruction;

apply a weighting function to said conjugate samples to reduce image artifacts; and reconstruct at least one image of the object.

16. A processor in accordance with claim 15 wherein said processor further configured to determine said plane of reconstruction to correspond to at least one of a piecewise straight line and a curve.

17. A processor in accordance with claim 15 wherein said processor further configured to determine said linear plane of reconstruction according to the relationship:

$$\beta = \beta_k - \alpha\gamma,$$

where $\beta$ is said plane of reconstruction, $\beta_k$, represents a projection angle at which a detector row k intersects said plane of reconstruction when $\gamma=0$, $\alpha$ is a value that ensures said plane of reconstruction and said conjugate sample line do not intersect, and $\alpha$ is defined as $\alpha \geq 1 - \pi/(2Q\gamma_m)$, where Q is a helical pitch, $\gamma_m$ is a maximum detector angle, and $\gamma$ is a detector angle.

18. A processor in accordance with claim 15 wherein said processor further configured to determine said conjugate sample line according to the relationship:

$$\beta' = \beta_k \pm \pi - (2-\alpha)\gamma,$$

where $\beta'$ is said conjugate sample line, $\beta_k$ represents the projection angle at which the detector row k intersects said plane of reconstruction when $\gamma=0$, $\alpha$ is a value that ensures said plane of reconstruction and said conjugate sample line do not intersect, and $\alpha$ is defined as $\alpha \geq 1 - \pi/(2Q\gamma_m)$, where Q is a helical pitch, $\gamma_m$ is a maximum detector angle, and $\gamma$ is a detector angle.

19. A processor in accordance with claim 15 wherein said processor further configured to determine a weight according to the relationship:

$$w_k(\gamma,\beta) = \begin{cases} \dfrac{\eta_k[\beta - \beta_{1,k}(\gamma,\beta)]}{\beta_{0,k}(\gamma,\beta) - \beta_{1,k}(\gamma,\beta)}, & \beta_{1,k}(\gamma,\beta) \leq \beta < \beta_{0,k}(\gamma,\beta) \\ \dfrac{\eta_k[\beta_{2,k}(\gamma,\beta) - \beta]}{\beta_{2,k}(\gamma,\beta) - \beta_{0,k}(\gamma,\beta)}, & \beta_{0,k}(\gamma,\beta) \leq \beta < \beta_{2,k}(\gamma,\beta), \\ 0, & \text{otherwise} \end{cases}$$

where $w_k(\gamma,\beta)$ is said helical weight; $\beta_{0,k}(\gamma,\beta)$ is the POR for detector row k; $\beta_{1,k}(\gamma,\beta)$ is a sample collected before $\beta_{0,k}(\gamma,\beta)$ and represents a value on detector row k that is a conjugate to the POR of another row; $\beta_{2,k}(\gamma,\beta)$ for k=0, ... 7, is collected after $\beta_{0,k}(\gamma,\beta)$ and is a sample on detector row k that is the conjugate to the POR of another row; $\eta_k$ is a row dependent scaling factor equal to 0.5 for k=0 and k=7; the center view of reconstruction is defined as $\beta=0$, and Q is a helical pitch. For other k values, $\eta_k$ equals 1.

20. A processor in accordance with claim 19 wherein said processor further configured to apply a weighting function according to the relationship:

$$\theta_k(\gamma,\beta) = 3w_k^2(\gamma,\beta) - 2w_k^3(\gamma,\beta),$$

where $\theta_k(\gamma,\beta)$ is said helical weighting function, and $w_k(\gamma,\beta)$ is said helical weight.

21. A -computer-readable medium in an imaging system, said computer-readable medium comprising:

records of projection data used to define a plane of reconstruction;

a plurality of rules to define a plane of reconstruction such that a conjugate sample line based on a plurality of records of conjugate samples does not intersect the plane of reconstruction;

a plurality of rules to determine a weighting function that is applied to the conjugate samples; and a plurality of rules to reconstruct an image.

22. A computer-readable medium according to claim 21 wherein the plane of reconstruction comprises a at least one of a linear relationship, a piecewise straight line, and a curve.

23. A computer-readable medium according to claim 22 wherein the linear plane of reconstruction comprises the relationship:

$$\beta = \beta_k - \alpha\gamma,$$

where $\beta$ is the plane of reconstruction, $\beta_k$, represents a projection angle at which a detector row k intersects said plane of reconstruction when γ=0, α is a value that ensures said plane of reconstruction and said conjugate sample line do not intersect, and α is defined as α≧1−π/(2Qγ$_m$), where Q is a helical pitch, γ$_m$ is a maximum detector angle, and γ is a detector angle.

24. A computer-readable medium according to claim 21 wherein the conjugate sample line comprises the relationship:

$$\beta' = \beta_k \pm \pi - (2-\alpha)\gamma,$$

where β' is a conjugate sample line, β$_k$ represents the projection angle at which the detector row k intersects said plane of reconstruction when γ=0, α is a value that ensures said plane of reconstruction and said conjugate sample line do not intersect, and α is defined as α≧1−π/(2Qγ$_m$), where Q is a helical pitch, γ$_m$ is a maximum detector angle, and γ is a detector angle.

25. A computer-readable medium according to claim 21 wherein the weighting function comprises a helical weight according to the relationship:

$$w_k(\gamma, \beta) = \begin{cases} \dfrac{\eta_k[\beta - \beta_{1,k}(\gamma, \beta)]}{\beta_{0,k}(\gamma, \beta) - \beta_{1,k}(\gamma, \beta)}, & \beta_{1,k}(\gamma, \beta) \leq \beta < \beta_{0,k}(\gamma, \beta) \\ \dfrac{\eta_k[\beta_{2,k}(\gamma, \beta) - \beta]}{\beta_{2,k}(\gamma, \beta) - \beta_{0,k}(\gamma, \beta)}, & \beta_{0,k}(\gamma, \beta) \leq \beta < \beta_{2,k}(\gamma, \beta), \\ 0, & \text{otherwise} \end{cases}$$

where $w_k(\gamma,\beta)$ is said helical weight; $\beta_{0,k}(\gamma,\beta)$ is the POR for detector row k; $\beta_{1,k}(\gamma,\beta)$ is a sample collected before $\beta_{0,k}(\gamma,\beta)$ and represents a value on detector row k that is a conjugate to the POR of another row; $\beta_{2,k}(\gamma,\beta)$ for k=0, . . . 7, is collected after $\beta_{0,k}(\gamma,\beta)$ and is a sample on detector row k that is the conjugate to the POR of another row; $\eta_k$ is a row dependent scaling factor equal to 0.5 for k=0 and k=7; the center view of reconstruction is defined as β=0, and Q is a helical pitch. For other k values, $\eta_k$ equals 1.

26. A computer-readable medium in accordance with claim 21 wherein said weighting function comprises the relationship:

$$\theta_k(\gamma,\beta) = 3w_k^2(\gamma,\beta) - 2w_k^3(\gamma,\beta),$$

where $\theta_k(\gamma,\beta)$ is said weighting function, and $w_k(\gamma,\beta)$ is said helical weight.

27. An imaging system comprising a computer, a gantry having a detector array, an x-ray source for radiating an x-ray beam along an imaging plane toward a detector array including a plurality of detector cells, the computer coupled to the x-ray source and the gantry, said imaging system configured to:
  scan an object to acquire a plurality of projection views of an object;
  define a plane of reconstruction comprising at least one of a linear relationship, a piecewise straight line, and a curve such that a conjugate sample line does not intersect said plane of reconstruction when using a mathematical relationship between a projection angle, detector rows, and detector angles;
  apply a helical weighting function to said conjugate samples to reduce image artifacts; and
  reconstruct at least one image of the object.

28. An imaging system in accordance with claim 27 wherein said imaging system further configured to determine said linear plane of reconstruction according to the relationship:

$$\beta = \beta_k - \alpha\gamma,$$

where β is the plane of reconstruction, β$_k$, represents a projection angle at which a detector row K intersects said plane of reconstruction when γ=0, α is a value that ensures said plane of reconstruction and said conjugate sample line do not intersect, and α is defined as α≧1−π/(2Qγ$_m$), where Q is a helical pitch, γ$_m$ is a maximum detector angle, and γ is a detector angle.

29. An imaging system in accordance with claim 27 wherein said imaging system further configured to determine said conjugate sample line according to the relationship:

$$\beta = \beta_k \pm \pi - (2-\alpha)\gamma,$$

where β' is a conjugate sample line, β$_k$ represents the projection angle at which the detector row k intersects said plane of reconstruction when γ=0, α is a value that ensures said plane of reconstruction and said conjugate sample line do not intersect, and α is defined as α≧1−π/(2Qγ$_m$), where Q is a helical pitch, γ$_m$ is a maximum detector angle, and γ is a detector angle.

30. An imaging system in accordance with claim 27 wherein said weighting function comprises a helical weight according to the relationship:

$$w_k(\gamma, \beta) = \begin{cases} \dfrac{\eta_k[\beta - \beta_{1,k}(\gamma, \beta)]}{\beta_{0,k}(\gamma, \beta) - \beta_{1,k}(\gamma, \beta)}, & \beta_{1,k}(\gamma, \beta) \leq \beta < \beta_{0,k}(\gamma, \beta) \\ \dfrac{\eta_k[\beta_{2,k}(\gamma, \beta) - \beta]}{\beta_{2,k}(\gamma, \beta) - \beta_{0,k}(\gamma, \beta)}, & \beta_{0,k}(\gamma, \beta) \leq \beta < \beta_{2,k}(\gamma, \beta), \\ 0, & \text{otherwise} \end{cases}$$

where $w_k(\gamma,\beta)$ is said helical weight; $\beta_{0,k}(\gamma,\beta)$ is the POR for detector row k; $\beta_{1,k}(\gamma,\beta)$ is a sample collected before $\beta_{0,k}(\gamma,\beta)$ and represents a value on detector row k that is a conjugate to the POR of another row; $\beta_{2,k}(\gamma,\beta)$ for k=0, . . . 7, is collected after $\beta_{0,k}(\gamma,\beta)$ and is a sample on detector row k that is the conjugate to the POR of another row; $\eta_k$ is a row dependent scaling factor equal to 0.5 for k=0 and k=7; the center view of reconstruction is defined as β=0, and Q is a helical pitch. For other k values, $\eta_k$ equals 1.

31. An imaging system in accordance with claim 27 wherein said helical weighting function comprises the relationship:

$$\theta_k(\gamma,\beta) = 3w_k^2(\gamma,\beta) - 2w_k^3(\gamma,\beta),$$

where $\theta_k(\gamma,\beta)$ is said helical weighting function, and $w_k(\gamma,\beta)$ is said helical weight.

* * * * *

UNITED STATES PATENT AND TRADEMARK OFFICE
CERTIFICATE OF CORRECTION

PATENT NO. : 6,452,996 B1
DATED : September 17, 2002
INVENTOR(S) : Jiang Hsieh

It is certified that error appears in the above-identified patent and that said Letters Patent is hereby corrected as shown below:

Column 8,
Line 25, deelte "helical pitch. For" and insert therefor -- helical pitch; for --.

Column 9,
Line 7, delete "$\beta = \beta_k \pm \pi - (2-\alpha)\gamma$," and insert therefor -- $\beta' = \beta_k \pm \pi - (2-\alpha)\gamma$, --.
Line 34, delete "helical pitch. For" and insert therefor -- helical pitch; for --.
Line 34, delete "$\eta_{k\ equals}$ 1." and insert therefor -- $\eta_k$ equals 1. --.

Column 10,
Line 10, delete "$\beta = \beta_k \pm \pi - (2-\alpha)\gamma$," and insert therefor -- $\beta' = \beta_k \pm \pi - (2-\alpha)\gamma$, --.
Line 38, delete "helical pitch. For" and insert therefor -- helical pitch; for --.
Line 45, delete "A -computer" and insert therefor -- A computer --.
Line 58, delete "comprises a at least" and insert therefor -- comprises at least --.

Column 11,
Line 9, delete "$\beta = \beta_k \pm \pi - (2-\alpha)\gamma$," and insert therefor -- $\beta' = \beta_k \pm \pi - (2-\alpha)\gamma$, --.
Line 36, delete "helical pitch. For" and insert therefor -- helical pitch; for --.

Column 12,
Line 9, delete "detector row K intersects" and insert therefor -- detector row k intersects --.
Line 21, delete "$\beta = \beta_k \pm \pi - (2-\alpha)\gamma$," and insert therefor -- $\beta' = \beta_k \pm \pi - (2-\alpha)\gamma$, --.
Line 49, delete "helical pitch. For" and insert therefor -- helical pitch; for --;

Signed and Sealed this

Twenty-fifth Day of May, 2004

JON W. DUDAS
*Acting Director of the United States Patent and Trademark Office*